Figures 1, 3:
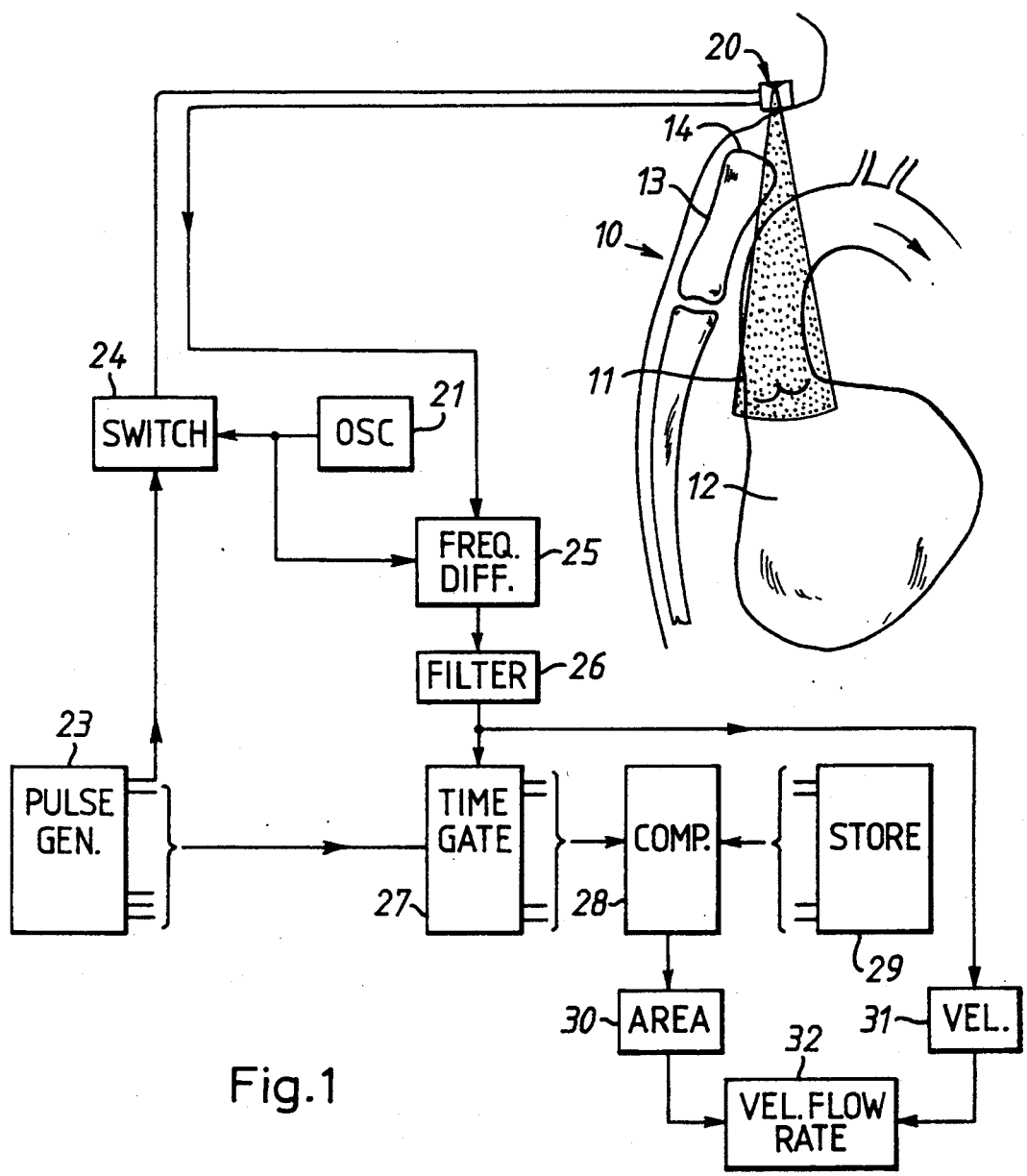

United States Patent [19]

Skidmore

[11] Patent Number: 5,406,948
[45] Date of Patent: Apr. 18, 1995

[54] FLOWMETERS

[75] Inventor: Robert Skidmore, Bristol, England

[73] Assignee: British Technology Group Ltd., London, England

[21] Appl. No.: 140,169

[22] PCT Filed: Jun. 12, 1992

[86] PCT No.: PCT/GB92/01061
§ 371 Date: Nov. 5, 1993
§ 102(e) Date: Nov. 5, 1993

[87] PCT Pub. No.: WO92/22248
PCT Pub. Date: Dec. 23, 1992

[30] Foreign Application Priority Data

Jun. 14, 1991 [GB] United Kingdom ............... 9112854

[51] Int. Cl.$^6$ .............................................. A61B 8/00
[52] U.S. Cl. ........................... 128/661.10; 73/861.25
[58] Field of Search ...................... 128/661.08, 661.09, 128/661.10, 662.01, 662.04, 661.04; 73/861.25

[56] References Cited

U.S. PATENT DOCUMENTS

| | | |
|---|---|---|
| 3,888,238 | 6/1975 | Meindl et al. |
| 4,476,874 | 10/1984 | Taenzer et al. |
| 4,493,216 | 1/1985 | Hassler. |
| 4,757,822 | 7/1988 | Di Giuliomaria et al. |
| 4,796,634 | 1/1989 | Huntsman et al. ............ 128/662.01 |
| 4,807,636 | 2/1989 | Skidmore et al. ............ 128/661.10 |
| 5,052,395 | 10/1991 | Burton et al. ............ 128/661.08 |
| 5,085,220 | 2/1992 | Nudell et al. ............ 128/662.04 |

FOREIGN PATENT DOCUMENTS

| | | |
|---|---|---|
| 0035325 | 9/1981 | European Pat. Off. |
| WO8603593 | 6/1986 | European Pat. Off. |
| 1507603 | 4/1978 | United Kingdom. |
| 2047404 | 11/1980 | United Kingdom. |
| 2070771 | 8/1984 | United Kingdom. |

OTHER PUBLICATIONS

WO, A904 634 (Waters Instruments Inc.) 1 Jun. 1989.
IEEE Transactions On Ultrasonics, Ferroelectrics and Frequncy Control, vol. 37, No. 3, May 1990, New York U.S. pp. 176–189; P. M. Embree et al, see pp. 181–185.
WO,A,8 303 000 (The Board Of Trustees Of The Leland Stanford Junior University) 1 Sep. 1983 see p. 9, line 7–line 18; Fig. 1–10.
D. H. Evans et al "Physics, Instrumentation and Clinical Application" Doppler Ultrasound, Feb. 1989, pp. 100–102.

Primary Examiner—George Manuel
Attorney, Agent, or Firm—Cushman, Darby & Cushman

[57] ABSTRACT

A method and apparatus for measuring the cross-sectional area of blood vessels, particularly the ascending aorta, is provided. An ultrasound probe (20) producing a divergent beam is directed downwardly via the suprasternal notch (14) and Doppler signals from the moving blood in the aorta (11) are detected. Signal processing means determine the Doppler power at successive ranges and the resulting power curve is correlated against stored curves representing a range of known aorta cross-sectional areas to find the closest fit. The velocity is also measured from the Doppler signal and hence the cardiac output can be determined.

14 Claims, 2 Drawing Sheets

FLOWMETERS

This invention concerns flowmeters and more particularly flowmeters of Doppler ultrasound form.

Flowmeters of this last form are routinely used in medical practice for the purposes of blood flow measurement. These meters are usually designed for transcutaneous application, but some have been developed for catheterised application into a blood vessel of interest. However, such meters are often limited to the provision of measures only of blood velocity, and commonly so in the case of catheter flowmeters, whereas the medical community frequently has an interest in knowing the blood volume flow rate in the relevant vessel. This interest extends particularly to the case in which the vessel is the aorta because the rate is then an effectively direct indication of cardiac power output. In any event, although blood velocity may be measured without undue difficulty and blood volume flow rate is provided simply as the product of velocity and vessel cross-sectional area, an indication of the area in question is not readily attained. Indeed in the case of the interest in cardiac output, area is often estimated for a given patient by way of a quite separate imaging procedure.

An object of the present invention is to improve this situation and to this end there is provided a method for measuring the cross-sectional area of a conduit through which fluid is flowing, which method comprises projecting a diverging ultrasound beam along the conduit and detecting the resulting Doppler signals from a plurality of successive ranges including one where the beam has diverged at least to the boundary of the conduit, producing for said ranges respective representations of the power of the associated Doppler signals and providing a representation of the cross-sectional area of the conduit by comparison of said power representations with stored predetermined data.

Clearly the conduit can be a blood vessel and, more particularly, the aorta and, in this particular case, the beam is conveniently directed transcutaneously by way of the suprasternal notch to pass longitudinally down the ascending aorta.

In a preferred form, the presently proposed method also entails determination of a measurement of the fluid flow velocity in the conduit by way of the Doppler signals, and preferably by reference to such signals at a range from the beam origin at least that of said one range.

The invention also provides, in another aspect from the presently proposed method, apparatus for carrying out such a method.

Figure 2:
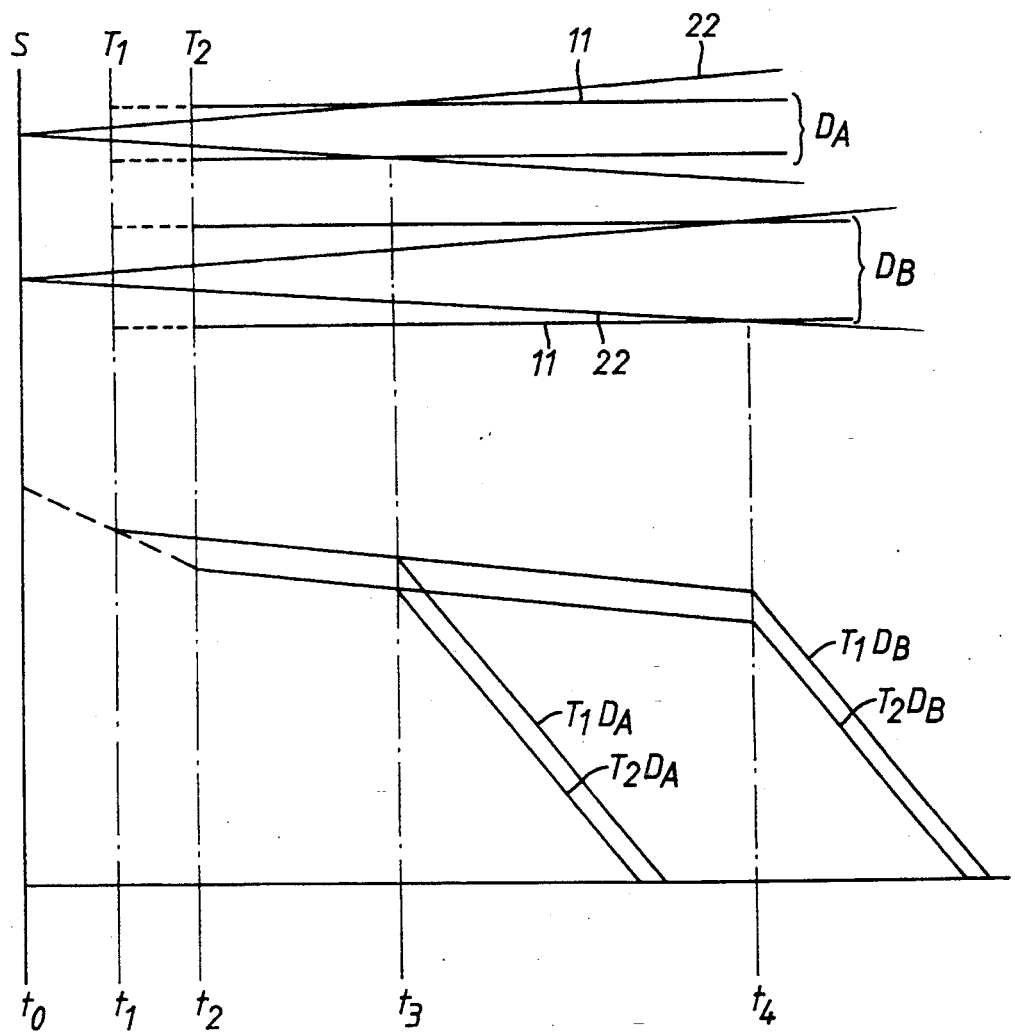

In order to clarify the invention as so far expressed, the same will now be described, by way of example, with reference to the accompanying drawings, in which:

FIG. 1 schematically illustrates one form of the invention;

FIG. 2 graphically illustrates in an idealised manner the operational basis for the invention;

FIG. 3 diagrammatically illustrates a form of a detail of the invention; and

Figure 4:
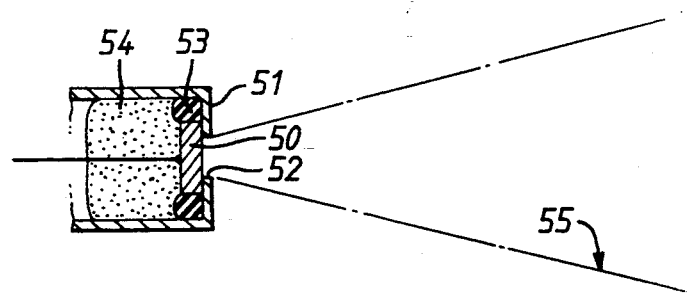

FIG. 4 illustrates an alternative form of a detail of the invention.

In FIG. 1 the invention is illustrated for use relative to a patient's body denoted in part at 10, with the aorta, heart, sternum and suprasternal notch indicated respectively at 11–14 within the body.

Apparatus according to the invention in FIG. 1 comprises an ultrasound transducer 20 operable in a transmission mode in response to an oscillator 21 to project a divergent beam 22 into the body 10. When the transducer is suitably located, the beam passes through the body tissue above the suprasternal notch and then longitudinally down the ascending aorta until the beam divergence is such that, at one range along the beam path, all of the blood flow through the aorta is isonated. Thereafter the beam diverges increasingly into the body tissue around the aorta.

This transmission operation is conducted in a pulsed manner under the control of an output from a pulse generator 23 which opens and closes switch 24 between the oscillator and transducer.

The transducer is also operable between transmission pulses in a receiver mode to detect returning signals which return along the beam path. The resultant output signal from the transducer is subject to three operations which are conducted serially in any suitable sequence. As shown in the example of FIG. 1 the signal is first applied, together with the output from oscillator 21, to a frequency difference circuit 25 to provide an output signal representing only Doppler components of the returning signals, that is to say, signals from surfaces which are moving relative to the transducer. These components will be predominantly from the blood corpuscles moving through the aorta, but some can arise from tissue surfaces moving due to respiratory or cardiac functions. These last components will be of a significantly lesser difference frequency than those due to blood flow and, as a second operation, are removed by way of an appropriate filter 26. Thirdly, the Doppler signal is time-gated at 27, under the control of a sequence of further pulse outputs produced by generator 23 between each successive pair of transducer transmission pulses, to present a series of signals representing the Doppler signals from successive ranges along the beam path. Particular variations of the signal processing system will not be described here in detail as such systems have been developed for use in Doppler ultrasound techniques and are generally well known. For example, a multigate system may be used to obtain information at the different ranges along the beam simultaneously, for example using parallel signal processing or using a serial digital signal processing system. Details of such systems are described in 'Doppler Ultrasound—Physics, Instrumentation and Clinical Applications' by D. H. Evans, W. N. McDicken, R. Skidmore and J. P. Woodcock (John Wiley & Sons 1989).

In the result signals are produced representing the Doppler signal power characteristic of the beam due to blood flow at a succession of ranges along the beam path.

This characteristic is compared, by way of a correlator 28, say, with similar characteristic representations of predetermined form associated with specific aortic cross-sectional areas and held in a store 29. The comparator provides at 30 a signal representing the area of the characteristic in the store best matched by that from the transducer.

In a separate operation the final time-gated output, or at least that at the one or subsequent range at which the blood flow is wholly isonated, is applied to a circuit 31 of a form to provide a signal representative of the mean blood velocity through the aorta.

This last velocity signal is combined with that representing cross-sectional area in a multiplier 32 to indicate cardiac output.

It may be required to determine the maximum blood flow in the ascending aorta in order to give a measurement of cardiac output at peak systole. This can be done by using the velocity signal to indicate the moment in time when a maximum velocity has been reached over the cardiac cycle, and automatically obtaining the signal representing cross-sectional area at that moment. Since the aortic diameter varies over the cardiac cycle this will represent an area larger than the mean cross-sectional area of the vessel. Multiplying the peak velocity measurement with this cross-sectional area measurement will thereby give a representation of peak systolic cardiac output. Variations in the individual measurements made at this point in the cycle can be allowed for by systolic coherent averaging, in which signals are averaged over, say, 10 heart-beats at systole.

The provision of the velocity signal can be effected in circuit 31 in known manner, but the basis for cross-sectional area determination requires clarification and this is given with reference to FIG. 2.

FIG. 2 graphically illustrates in an idealised manner four different situations for a given beam passing from the skin S through tissue of thickness $T_1$ or $T_2$ into an aorta of diameter $D_A$ or $D_B$ and the resultant Doppler signal power characteristics due to blood flow.

A general point to note for each situation is that there is no Doppler blood signal, but there will be some beam attenuation, while the beam passes through the tissue. Accordingly each characteristic commences with a declining portion distinctively indicated in broken line form. This portion will of course occur for a period dependent on the tissue thickness and this is denoted as time $t_1$ and $t_2$ respectively for thicknesses $T_1$ and $T_2$ relative to a transmission pulse occurring at time $t_0$.

Doppler blood signals are initiated when the beam enters the aorta and this is indicated by presentation of the related power characteristic in solid line form. Also the characteristic continues to decline due to attenuation, but at a reduced rate as the attenuation in blood is less than that in tissue.

The beam is of course diverging and a point is reached, namely the one range referred to above, at which the whole of the cross section of the aorta is isonated and the beam thereafter passes increasingly through tissue again. This gives rise to a markedly discontinuous downturn in the characteristic because, although the aorta is still wholly isonated, a progressively decreasing proportion of the beam power is involved. In any event this discontinuity will occur at a time and range which depends on the cross-sectional diameter and this is denoted at times $t_3$ and $t_4$ respectively for diameters $D_A$ and $D_B$.

In the result it will be seen that each different situation gives rise to a uniquely related characteristic such as $T_1D_A$ to $T_2D_B$ and, even though idealised in a simple manner, this holds in reality sufficient for the present purpose. Thus, it is possible to compare an actual characteristic with predetermined forms and thereby determine the diameter, or cross-sectional area, the two being essentially synonymous, as it were, assuming circular cross section. The comparison with predetermined data is preferably carried out after normalising the obtained power characteristic, for example the normalisation is such that the initial signal value when the beam enters the aorta (at point $t_1$ or $t_2$ in FIG. 2) is set at a nominal value of 1.0. Correlation means then use the predetermined data to ascertain the probability that the actual characteristic was obtained from a vessel with one of a finite range of cross-sectional areas, and the cross-sectional area selected is that corresponding to the highest probability. This does not require an impracticable storage requirement for the predetermined forms as the aortic diameter can sensibly be viewed as having a finite range extending over about 13 mm between minimum and maximum, and an accuracy of no less than 1 mm is clinically adequate.

FIG. 3 diagrammatically illustrates a preferred transducer arrangement suitable for use with the present invention.

As is evident from the above discussion the invention rests on the provision of a divergent beam. This can lead to complexity in that, conventionally, this would be seen to require a convexly shaped transducer or a flat disc transducer in association with an appropriate lens. Moreover, with such arrangements, separate measures will be needed in respect of providing operational modes for transmission and reception.

As indicated in FIG. 3, it is proposed that the transducer 40 be of composite flat form with a central disc 41 and a surrounding annulus 42. This transducer is operated by way of a transformer which, from a transmission point of view, has a primary winding 43 and two secondary windings 44,45, the secondary windings being oppositely wound with that, 44, wound in common with the primary being connected with central disc 41, and the other secondary winding being connected with the surrounding annulus 42. The same transformer arrangement also serves for reception.

An alternative transducer arrangement is illustrated diagrammatically in FIG. 4. This employs a single piezoelectric element 50 mounted within a housing 51 adjacent to an aperture 52 in the end wall of the housing. The housing is preferably of cylindrical form, fabricated from metal, such as brass. The piezoelectric element is fixedly mounted in place by epoxy resin 53 and the housing may also contain a volume of damping material 54. The shape of the transmission field depends on the size of the aperture 52, a wider divergent field being produced as the aperture diameter is reduced. The transmission field is represented diagrammatically at 55.

I claim:

1. A method for measuring the cross-sectional area of a conduit through which fluid is flowing, using stored predetermined data representative of respective power characteristics associated with specific conduit cross-sectional areas, comprising the steps of:

projecting a diverging ultrasound beam along the conduit and detecting the resulting Doppler signals from a plurality of successive ranges including one where the beam has diverged at least to the boundary of the conduit, producing for said ranges respective representations of the power of the associated Doppler signals, and providing a representation of the cross-sectional area of the conduit by comparison of said power representations with said stored predetermined data.

2. A method according to claim 1 in which the conduit is a blood vessel.

3. A method according to claim 2 in which the beam is directed transcutaneously.

4. A method according to claim 3 in which the conduit is the ascending aorta and the beam is directed by way of the suprasternal notch.

5. A method according to any preceding claim in which said power representations are normalised with respect to a reference datum and correlated against power representations of a similar form representing said stored predetermined data.

6. A method according to claim 1 in which a measurement of the fluid flow velocity in the conduit is made from the Doppler signals from said one range where the beam has diverged at least to the boundary of the conduit.

7. A method according to claim 6 in which the fluid flow velocity measurement is multiplied by the cross-sectional area as measured to determined fluid volume flow.

8. A method according to claim 6 or 7 in which the fluid flow velocity measurement is used to determine a moment of peak flow within the conduit and the measurement of cross-sectional area is obtained at this same moment.

9. Apparatus for carrying out measurement of the cross-sectional area of a conduit through which fluid is flowing comprising:
   means for storing predetermined data representative of respective power characteristics associated with specific conduit cross-sectional areas;
   an ultrasound transducer operable in a transmission mode to project a divergent beam along the conduit;
   a receiver to detect returning signals;
   signal processing means for producing a representation of the Doppler signal power characteristic of the beam due to fluid flow at a succession of ranges along the beam path; and
   means for comparing said representation with said stored predetermined data to obtain a representation of the cross-sectional area of the conduit.

10. Apparatus according to claim 9 in which a single transducer operates as both transmitter and receiver, the transducer being operated in a pulsed manner.

11. Apparatus according to claim 9 or 10 in which said signal processing means comprise:
    means for providing a signal representing only Doppler components of the returning signals which are associated with the movement of fluid within the conduit; and
    means for time-gating the signal provided to produce a set of Doppler power representations from successive ranges along the beam path.

12. Apparatus according to claim 11 in which the Doppler signal is multigated to provide simultaneous signals from the plurality of ranges along the beam path.

13. Apparatus according to claim 9 in which the transducer producing the divergent ultrasound beam comprises a piezoelectric element within a cylindrical housing, the element being mounted adjacent to an aperture in an end wall of the housing.

14. Apparatus according to claim 9 in which the transducer producing the divergent ultrasound beam comprises a central element and a surrounding substantially concentric annular element, the two elements being driven in antiphase.

* * * * *